(12) United States Patent
Baldwin et al.

(10) Patent No.: US 6,914,114 B2
(45) Date of Patent: Jul. 5, 2005

(54) ABSORBING COMPOUNDS FOR SPIN-ON-GLASS ANTI-REFLECTIVE COATINGS FOR PHOTOLITHOGRAPHY

(75) Inventors: Teresa Baldwin, Fremont, CA (US); Mary Richey, Santa Clara, CA (US); James S. Drage, Fremont, CA (US); Hui-Jung Wu, Fremont, CA (US); Richard Spear, San Jose, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/428,807

(22) Filed: Apr. 30, 2003

(65) Prior Publication Data

US 2003/0199659 A1 Oct. 23, 2003

Related U.S. Application Data

(62) Division of application No. 10/012,651, filed on Nov. 5, 2001, now Pat. No. 6,605,362, which is a division of application No. 09/617,365, filed on Jul. 17, 2000, now Pat. No. 6,368,400.

(51) Int. Cl.$^7$ .............................................. C08G 77/00
(52) U.S. Cl. .................. 528/43; 556/458; 552/208; 552/209; 552/271; 528/34; 528/39; 525/477
(58) Field of Search ............................ 528/43, 34, 39; 525/477; 556/458; 552/208, 209, 271

(56) References Cited

U.S. PATENT DOCUMENTS

| | | | |
|---|---|---|---|
| 3,615,272 A | 10/1971 | Collins ........................ 23/366 |
| 3,873,361 A | 3/1975 | Franco et al. ............... 117/212 |
| 3,884,702 A | 5/1975 | Koshimo et al. ............. 96/115 |
| 4,053,313 A | 10/1977 | Fan ................................ 96/36 |
| 4,257,826 A | 3/1981 | Matalone, Jr. ............... 148/1.5 |
| 4,290,896 A | 9/1981 | Gordon et al. .............. 210/710 |

(Continued)

FOREIGN PATENT DOCUMENTS

| | | |
|---|---|---|
| AU | 8322233 | 6/1984 |
| AU | 8537628 | 9/1985 |
| BE | 901479 | 5/1985 |
| BR | 8108625 | 4/1982 |
| CA | 1162666 | 2/1984 |
| CA | 1204543 | 5/1986 |
| CA | 1245394 | 11/1988 |
| CA | 2027031 | 4/1991 |
| CA | 1284748 | 6/1991 |
| CA | 2034908 | 8/1991 |
| CH | 667097 | 9/1988 |

(Continued)

OTHER PUBLICATIONS

Isumi, et al.; Hydrosilylation of Carbonyl Compounds Catalyzed by Solid Acids and Bases, Tetrahedron Letters, vo. 32, No. 36, pp. 4741–4744, (1991).

(Continued)

*Primary Examiner*—Kuo-Liang Peng
(74) *Attorney, Agent, or Firm*—Bingham McCutchen; Sandra P. Thompson

(57) ABSTRACT

An absorbing ether-like compound including a siliconethoxy, silicondiethoxy, or silicontriethoxy species attached to a naphthalene or anthracene chromophore via an oxygen linkage is used as an organic light-absorbing compound. The absorbing ether-like compound is incorporated into spin-on glass materials to provide anti-reflective coating materials for deep ultraviolet photolithography. A method of synthesizing the light-absorbing ether compounds is based on the reaction of an alcohol-substituted chromophore with an acetoxysilicon compound in the presence of alcohol. A method of making absorbing spin-on-glass materials including the absorbing ether-like compounds is also provided.

16 Claims, 1 Drawing Sheet

U.S. PATENT DOCUMENTS

| | | | |
|---|---|---|---|
| 4,312,970 A | 1/1982 | Gaul, Jr. | 526/279 |
| 4,328,262 A | 5/1982 | Kurahashi et al. | 427/93 |
| 4,349,609 A | 9/1982 | Takeda et al. | 428/429 |
| 4,399,266 A | 8/1983 | Matsumura et al. | 528/10 |
| 4,413,052 A | 11/1983 | Green et al. | 430/327 |
| 4,419,437 A | 12/1983 | Noonan et al. | 430/270 |
| 4,423,135 A | 12/1983 | Chen et al. | 430/271 |
| 4,434,127 A | 2/1984 | Baile et al. | 264/236 |
| 4,483,107 A | 11/1984 | Tomoyori et al. | 51/281 |
| 4,510,283 A | 4/1985 | Takeda et al. | 524/356 |
| 4,513,132 A | 4/1985 | Shoji et al. | 528/21 |
| 4,515,828 A | 5/1985 | Economy et al. | 427/82 |
| 4,546,017 A | 10/1985 | Vitunic | 326/30 |
| 4,600,685 A | 7/1986 | Kitakohji et al. | 430/313 |
| 4,603,168 A | 7/1986 | Sasaki et al. | 522/18 |
| 4,617,252 A | 10/1986 | Cordes, III et al. | 430/272 |
| 4,626,556 A | 12/1986 | Nozue et al. | 522/99 |
| 4,657,843 A | 4/1987 | Fukuyama et al. | 430/323 |
| 4,657,965 A | 4/1987 | Watanabe et al. | 524/506 |
| 4,663,414 A | 5/1987 | Estes et al. | 528/30 |
| 4,670,299 A | 6/1987 | Fukuyama et al. | 427/96 |
| 4,676,867 A | 6/1987 | Elkins et al. | 156/643 |
| 4,687,216 A | 8/1987 | Kawamoto et al. | 280/91 |
| 4,702,990 A | 10/1987 | Tanaka et al. | 430/197 |
| 4,723,978 A | 2/1988 | Clodgo et al. | 65/31 |
| 4,745,169 A | 5/1988 | Sugiyama et al. | 528/43 |
| 4,753,855 A | 6/1988 | Haluska et al. | 428/702 |
| 4,756,977 A | 7/1988 | Haluska et al. | 428/704 |
| 4,806,504 A | 2/1989 | Cleeves | 437/228 |
| 4,808,653 A | 2/1989 | Haluska et al. | 524/398 |
| 4,822,697 A | 4/1989 | Haluska et al. | 428/698 |
| 4,826,943 A | 5/1989 | Ito et al. | 528/21 |
| 4,847,162 A | 7/1989 | Haluska et al. | 428/457 |
| 4,849,296 A | 7/1989 | Haluska et al. | 428/457 |
| 4,855,199 A | 8/1989 | Bolon et al. | 430/18 |
| 4,863,833 A | 9/1989 | Fukuyama et al. | 430/286 |
| 4,895,914 A | 1/1990 | Saitoh et al. | 525/478 |
| 4,898,907 A | 2/1990 | Haluska et al. | 524/490 |
| 4,904,721 A | 2/1990 | Hanaoka et al. | 524/266 |
| 4,910,122 A | 3/1990 | Arnold et al. | 430/313 |
| 4,911,992 A | 3/1990 | Haluska et al. | 428/698 |
| 4,921,778 A | 5/1990 | Thackeray et al. | 430/326 |
| 4,935,320 A | 6/1990 | Rohde et al. | 430/14 |
| 4,973,526 A | 11/1990 | Haluska | 428/697 |
| 4,981,530 A | 1/1991 | Clodgo et al. | 148/33.3 |
| 4,988,514 A | 1/1991 | Fukuyama et al. | 428/447 |
| 4,999,397 A | 3/1991 | Weiss et al. | 524/755 |
| 5,008,320 A | 4/1991 | Haluska et al. | 524/361 |
| 5,043,789 A | 8/1991 | Linde et al. | 357/52 |
| 5,045,592 A | 9/1991 | Weiss et al. | 524/755 |
| 5,059,448 A | 10/1991 | Chandra et al. | 427/53.1 |
| 5,063,134 A | 11/1991 | Horiguchi et al. | 430/192 |
| 5,063,267 A | 11/1991 | Hanneman et al. | 524/284 |
| 5,684,095 A * | 11/1997 | Morimoto et al. | 525/438 |
| 6,165,697 A | 12/2000 | Thacharay et al. | 430/325 |
| 6,268,457 B1 | 7/2001 | Kennedy et al. | 528/39 |

FOREIGN PATENT DOCUMENTS

| | | |
|---|---|---|
| DD | 159202 | 2/1983 |
| DE | 3165340 | 9/1984 |
| DE | 3500979 | 7/1985 |
| DE | 3173441 | 2/1986 |
| DE | 3366387 | 10/1986 |
| DE | 3610462 | 10/1986 |
| DE | 3374204 | 12/1987 |
| DE | 3278567 | 6/1988 |
| DE | 3760773 | 11/1989 |
| DE | 3574418 | 12/1989 |
| DE | 3380961 | 1/1990 |
| DE | 3575156 | 2/1990 |
| DE | 3579630 | 10/1990 |
| DE | 3768663 | 4/1991 |
| EP | 40906 | 12/1981 |
| EP | 46695 | 3/1982 |
| EP | 0046695 | 3/1982 |
| EP | 76656 | 4/1983 |
| EP | 91104 | 10/1983 |
| EP | 111395 | 6/1984 |
| EP | 112168 | 6/1984 |
| EP | 0146411 | 6/1985 |
| EP | 0183382 | 6/1986 |
| EP | 202108 | 11/1986 |
| EP | 204963 | 11/1986 |
| EP | 163538 | 12/1986 |
| EP | 198976 | 12/1986 |
| EP | 0223987 | 6/1987 |
| EP | 229629 | 7/1987 |
| EP | 270229 | 7/1987 |
| EP | 270231 | 6/1988 |
| EP | 270263 | 6/1988 |
| EP | 270369 | 6/1988 |
| EP | 274428 | 7/1988 |
| EP | 323103 | 7/1989 |
| EP | 323186 | 7/1989 |
| EP | 326810 | 8/1989 |
| EP | 255303 | 10/1989 |
| EP | 371287 | 6/1990 |
| EP | 164598 | 9/1990 |
| EP | 0406911 | 1/1991 |
| EP | 0423446 | 4/1991 |
| EP | 427395 | 5/1991 |
| EP | 442632 | 8/1991 |
| EP | 447611 | 9/1991 |
| EP | 449263 | 10/1991 |
| EP | 0401499 | 12/1999 |
| ES | 2005468 | 3/1989 |
| ES | 2005469 | 3/1989 |
| ES | 2010233 | 11/1989 |
| ES | 2010234 | 11/1989 |
| FR | 2558169 | 7/1985 |
| FR | 2579552 | 10/1986 |
| GB | 2152523 | 8/1985 |
| GB | 2173750 | 10/1988 |
| IT | 1184101 | 10/1987 |
| JP | 50022870 | 3/1975 |
| JP | 53000896 | 1/1978 |
| JP | 53088099 | 8/1978 |
| JP | 53124561 | 10/1978 |
| JP | 54079037 | 6/1979 |
| JP | 54083956 | 7/1979 |
| JP | 54083957 | 7/1979 |
| JP | 55000761 | 1/1980 |
| JP | 55165942 | 12/1980 |
| JP | 56000827 | 1/1981 |
| JP | 56000828 | 1/1981 |
| JP | 56081333 | 7/1981 |
| JP | 81028935 | 7/1981 |
| JP | 56118465 | 9/1981 |
| JP | 56129261 | 10/1981 |
| JP | 56139533 | 10/1981 |
| JP | 56151731 | 11/1981 |
| JP | 57006712 | 1/1982 |
| JP | 57008279 | 1/1982 |
| JP | 57038865 | 3/1982 |
| JP | 57040526 | 3/1982 |
| JP | 57059672 | 4/1982 |
| JP | 57500697 | 4/1982 |
| JP | 57083563 | 5/1982 |
| JP | 57112047 | 7/1982 |
| JP | 57125905 | 8/1982 |

| | | | | | |
|---|---|---|---|---|---|
| JP | 57131250 | 8/1982 | JP | 62096526 | 5/1987 |
| JP | 57141641 | 9/1982 | JP | 62096942 | 5/1987 |
| JP | 57141642 | 9/1982 | JP | 62106632 | 5/1987 |
| JP | 57168246 | 10/1982 | JP | 87028511 | 6/1987 |
| JP | 57168247 | 10/1982 | JP | 62159141 | 7/1987 |
| JP | 58013632 | 1/1983 | JP | 62161124 | 7/1987 |
| JP | 83007001 | 2/1983 | JP | 87034069 | 7/1987 |
| JP | 583249 | 4/1983 | JP | 62215944 | 9/1987 |
| JP | 5866335 | 4/1983 | JP | 62276543 | 12/1987 |
| JP | 58059222 | 4/1983 | JP | 62284352 | 12/1987 |
| JP | 58069217 | 4/1983 | JP | 62299965 | 12/1987 |
| JP | 59058054 | 4/1983 | JP | 63006544 | 1/1988 |
| JP | 58089641 | 5/1983 | JP | 88003893 | 1/1988 |
| JP | 58093240 | 6/1983 | JP | 63032543 | 2/1988 |
| JP | 58171416 | 10/1983 | JP | 63046272 | 2/1988 |
| JP | 58173174 | 10/1983 | JP | 88012899 | 3/1988 |
| JP | 58174480 | 10/1983 | JP | 63072745 | 4/1988 |
| JP | 84014263 | 4/1984 | JP | 88016424 | 4/1988 |
| JP | 59109565 | 6/1984 | JP | 88020450 | 4/1988 |
| JP | 59112487 | 6/1984 | JP | 63106649 | 5/1988 |
| JP | 59112834 | 6/1984 | JP | 63117074 | 5/1988 |
| JP | 59115356 | 7/1984 | JP | 63118739 | 5/1988 |
| JP | 59129230 | 7/1984 | JP | 63120774 | 5/1988 |
| JP | 59132424 | 7/1984 | JP | 63137972 | 6/1988 |
| JP | 59189126 | 10/1984 | JP | 63144524 | 6/1988 |
| JP | 59190211 | 10/1984 | JP | 63144525 | 6/1988 |
| JP | 84050182 | 12/1984 | JP | 63146303 | 6/1988 |
| JP | 84052678 | 12/1984 | JP | 63149636 | 6/1988 |
| JP | 84052893 | 12/1984 | JP | 63152130 | 6/1988 |
| JP | 60042426 | 3/1985 | JP | 88030947 | 6/1988 |
| JP | 60076528 | 5/1985 | JP | 63170476 | 7/1988 |
| JP | 60086017 | 5/1985 | JP | 63172757 | 7/1988 |
| JP | 60094412 | 5/1985 | JP | 63173382 | 7/1988 |
| JP | 85017312 | 5/1985 | JP | 63199251 | 8/1988 |
| JP | 85017335 | 5/1985 | JP | 63207839 | 8/1988 |
| JP | 60149626 | 8/1985 | JP | 63238133 | 10/1988 |
| JP | 60152552 | 8/1985 | JP | 88052058 | 10/1988 |
| JP | 60161457 | 8/1985 | JP | 63287823 | 11/1988 |
| JP | 85017214 | 8/1985 | JP | 63289045 | 11/1988 |
| JP | 60185892 | 9/1985 | JP | 63308077 | 12/1988 |
| JP | 60038422 | 10/1985 | JP | 88064771 | 12/1988 |
| JP | 60195148 | 10/1985 | JP | 88064772 | 12/1988 |
| JP | 60229945 | 11/1985 | JP | 1016868 | 1/1989 |
| JP | 60238827 | 11/1985 | JP | 64001769 | 1/1989 |
| JP | 60254034 | 12/1985 | JP | 1038256 | 2/1989 |
| JP | 60254035 | 12/1985 | JP | 1056710 | 3/1989 |
| JP | 60254036 | 12/1985 | JP | 1076046 | 3/1989 |
| JP | 60254132 | 12/1985 | JP | 1110546 | 4/1989 |
| JP | 61014096 | 1/1986 | JP | 1115966 | 4/1989 |
| JP | 6129153 | 2/1986 | JP | 1168718 | 7/1989 |
| JP | 86010496 | 3/1986 | JP | 1185367 | 7/1989 |
| JP | 61098755 | 5/1986 | JP | 1202826 | 8/1989 |
| JP | 61098764 | 5/1986 | JP | 1203013 | 8/1989 |
| JP | 61108628 | 5/1986 | JP | 1204043 | 8/1989 |
| JP | 86018945 | 5/1986 | JP | 1204432 | 8/1989 |
| JP | 61127732 | 6/1986 | JP | 1217352 | 8/1989 |
| JP | 61159754 | 7/1986 | JP | 89043773 | 9/1989 |
| JP | 61098747 | 8/1986 | JP | 1308429 | 12/1989 |
| JP | 61221232 | 10/1986 | JP | 1313942 | 12/1989 |
| JP | 61224330 | 10/1986 | JP | 2000615 | 1/1990 |
| JP | 61256347 | 11/1986 | JP | 2008209 | 1/1990 |
| JP | 61260242 | 11/1986 | JP | 02038427 | 2/1990 |
| JP | 61261370 | 11/1986 | JP | 2038427 | 2/1990 |
| JP | 86055524 | 11/1986 | JP | 2099955 | 4/1990 |
| JP | 61292342 | 12/1986 | JP | 2110464 | 4/1990 |
| JP | 62027417 | 2/1987 | JP | 2124936 | 5/1990 |
| JP | 62043426 | 2/1987 | JP | 2150426 | 6/1990 |
| JP | 62067561 | 3/1987 | JP | 2163744 | 6/1990 |
| JP | 87016212 | 4/1987 | JP | 90034983 | 8/1990 |
| JP | 87017629 | 4/1987 | JP | 2178330 | 9/1990 |
| JP | 62056956 | 5/1987 | JP | 90047102 | 10/1990 |

| | | |
|---|---|---|
| JP | 2308806 | 12/1990 |
| JP | 3007766 | 1/1991 |
| JP | 3026716 | 2/1991 |
| JP | 3028852 | 2/1991 |
| JP | 3031325 | 2/1991 |
| JP | 3041156 | 2/1991 |
| JP | 3045628 | 2/1991 |
| JP | 3047883 | 2/1991 |
| JP | 3059016 | 3/1991 |
| JP | 3064337 | 3/1991 |
| JP | 91015821 | 3/1991 |
| JP | 91019260 | 3/1991 |
| JP | 3154007 | 7/1991 |
| JP | 3162441 | 7/1991 |
| JP | 91044291 | 7/1991 |
| JP | 3183675 | 8/1991 |
| JP | 3197135 | 8/1991 |
| JP | 3207774 | 9/1991 |
| JP | 3252446 | 11/1991 |
| JP | 63005337 | 1/1998 |
| KR | 8800853 | 5/1988 |
| KR | 9002364 | 4/1990 |
| KR | 9005894 | 8/1990 |
| NL | 191061 | 8/1994 |
| NL | 8500065 | 8/1994 |
| SE | 8500137 | 7/1985 |
| SE | 458447 | 4/1989 |
| SU | 413850 | 3/1984 |
| WO | WO8103484 | 12/1981 |
| WO | WO90/03598 | 4/1990 |

OTHER PUBLICATIONS

Pacansky, et al. entitled "Photochemical Decomposition Mechanisms for AZ–Type Photoresists", Jan. 1979, pp. 42–55.

Korchkov, et al. entitled "Low Temperature Dielectric Films Form Octavinylsilsesquioxane", Dec. 1982, pp. 373–376.

Lavrent'yev, et al. entitled "Polyhedral Oligosilsesquioxanes and Their Homo Derivatives", Aug. 1981, pp. 199–236.

Lavrent'yev, et al. entitled "Ethylmethyloctasesquioxanes: Products of the Reactions of Ethylpolycyclosiloxanes with Tricholormethylsilane. Their Chromatographic Mass Spectrometric Investigation," 1981.

Li, et al. entitled "Organosiloxane Based Bottom Antireflective Coatings for 193nm Lithography", pp. 1–10.

Li, et al. entitled "An Organosiloxane Spin On Bottom Antireflective Coatings for ArF Lithography", pp. 1–9.

* cited by examiner

US 6,914,114 B2

ABSORBING COMPOUNDS FOR SPIN-ON-GLASS ANTI-REFLECTIVE COATINGS FOR PHOTOLITHOGRAPHY

This application is a divisional of application Ser. No. 10/012,651, filed Nov. 5, 2001, issued U.S. Pat. No. 6,605,362, which is a divisional of application Ser. No. 09/617,365, filed Jul. 17, 2000, issued U.S. Pat. No. 6,368,400.

TECHNICAL FIELD

The present invention relates generally to light-absorbing spin-on glass materials and more specifically to absorbing compounds that may be incorporated in spin-on glass materials for use as anti-reflective layers in photolithography and methods of producing the absorbing compounds.

BACKGROUND

To meet the requirements for faster performance, the characteristic dimensions of features of integrated circuit devices have continued to be decreased. Manufacturing of devices with smaller feature sizes introduces new challenges in many of the processes conventionally used in semiconductor fabrication. One of the most important of these fabrication processes is photolithography.

It has long been recognized that linewidth variations in patterns produced by photolithography can result from optical interference from light reflecting off an underlying layer on a semiconductor wafer. Variations in photoresist thickness due to the topography of the underlying layer also induce linewidth variations. Anti-reflective coatings (ARC) applied under a photoresist layer have been used to prevent interference from reflection of the irradiating beam. In addition, anti-reflective coatings partially planarize the wafer topography, helping to improve linewidth variation over steps because the photoresist thickness is more uniform.

Organic polymer films, particularly those that absorb at the i-line (365 nm) and g-line (436 nm) wavelengths conventionally used to expose photoresists, and at the recently used 248 nm wavelength, have been employed as anti-reflective coatings. However, the fact that the organic ARC's share many chemical properties with the organic photoresists can limit usable process sequences. Furthermore organic ARC's may intermix with photoresist layers. One solution to avoid intermixing, is to introduce thermosetting binders as additional components of organic ARC's, as described, for example in U.S. Pat. No. 5,693,691 to Flaim et al. Dyes may also be incorporated in organic ARC's, as well as, optionally, additional additives such as wetting agents, adhesions promoters, preservatives, and plasticizers, as described in U.S. Pat. No. 4,910,122 to Arnold et al.

Silicon oxynitride is another material that has been used as an anti-reflective coating. However, silicon oxynitride works as an ARC by a destructive interference process rather than by absorption, which means that very tight control of the oxynitride thickness is necessary and that the material may not work well as an ARC over highly variable topography. Furthermore silicon oxynitride is typically deposited by chemical vapor deposition, while photoresist layers are typically applied using a spin-coater. The additional chemical vapor deposition process can add to processing complexity.

Yet another class of materials that can be used as an anti-reflective layer is spin-on-glass (SOG) compositions containing a dye. Yau et al., U.S. Pat. No. 4,587,138, disclose a dye such as basic yellow #11 mixed with a spin-on-glass in an amount approximately 1% by weight. Allman et al. U.S. Pat. No. 5,100,503 disclose a cross-linked polyorganosiloxane containing an inorganic dye such as $TiO_2$, $Cr_2O_7$, $MoO_4$, $MnO_4$, or $ScO_4$, and an adhesion promoter. Allman additionally teaches that the spin-on-glass compositions also serve as a planarizing layer. However, the spin-on-glass, dye combinations that have been disclosed to date are not optimal for exposure to the deep ultraviolet, particularly 248 and 193 nm, light sources that are coming into use to produce devices with small feature sizes. In addition, not all dyes can be readily incorporated into an arbitrary spin-on-glass composition.

Thus there remains a need for compounds absorbing strongly in the deep ultraviolet spectral region that may be incorporated into spin-on-glass compositions to provide anti-reflective coatings and for methods of synthesizing such absorbing compounds.

SUMMARY

An anti-reflective coating material for deep ultraviolet photolithography includes one or more organic absorbing compounds incorporated into a spin-on-glass (SOG) material. According to an embodiment of the present invention, an absorbing ether-like compound including a siliconethoxy, silicondiethoxy, or silicontriethoxy species attached to a naphthalene or anthracene chromophore via an oxygen linkage is used as an organic absorbing compound. The absorbing ether-like compounds have a general formula $C_{14}H_9(CH_2)_nOSiR_m(OC_2H_5)_{3-m}$ or $C_{10}H_8(CH_2)_nOSiR_m(OC_2H_5)_{3-m}$, where n=1–3, m=0–2, and R is alkyl group such as a methyl, ethyl, or propyl group.

A method of synthesizing the light-absorbing ether-like compounds of the present invention is based on the reaction of an alcohol-substituted chromophore with an acetoxysilicon compound of the general formula $R_mSi(OCOCH_3)_{4-m}$, in the presence of a stoichiometric amount of alcohol, where the reactants have the molar ratio of 1:1:3-m. For example, the synthesis of 9-anthracene methoxy-methyldiethoxysilane uses 9-anthracene methanol, methyltriacetoxysilane (MTAS), and ethanol in a molar ratio of 1:1:2 as reactants. The reactants are combined with acetone, or a suitable alternative ketone, to form a reaction mixture which is stirred for an extended period sufficient to form the product, and then the acetic acid byproduct is removed by inert gas purging or by vacuum extraction.

The absorbing ether-like compounds may be incorporated into spin-on-glass materials including methylsiloxane, methylsilsesquioxane, phenylsiloxane, phenylsilsesquioxane, methylphenylsiloxane, methylphenylsilsesquioxane, and silicate polymers. As used herein, spin-on-glass materials also include hydrogensiloxane polymers of the general formula $(H_{0-1.0}SiO_{1.5-2.0})_x$ and hydrogensilsesquioxane polymers, which have the formula $(HSiO_{1.5})_x$, where x is greater than about 8. Also included are copolymers of hydrogensilsesquioxane and alkoxyhydridosiloxane or hydroxyhydridosiloxane. Spin-on-glass materials additionally include organohydridosiloxane polymers of the general formula $(H_{0-1.0}SiO_{1.5-2.0})_n(R'_{0-1.0}SiO_{1.5-2.0})_m$, and organohydridosilsesquioxane polymers of the general formula $(HSiO_{1.5})_n(R'SiO_{1.5})_m$, where m is greater than 0 and the sum of n and m is greater than about 8 and R' is alkyl or aryl. Coating solutions of spin-on-glass materials incorporating absorbing compounds are used to form anti-reflecting films on various layers in integrated circuit devices.

According to another aspect of the present invention, methods for synthesizing absorbing spin-on-glass compositions including the absorbing ether compounds are also provided.

DETAILED DESCRIPTION

Figure 1:
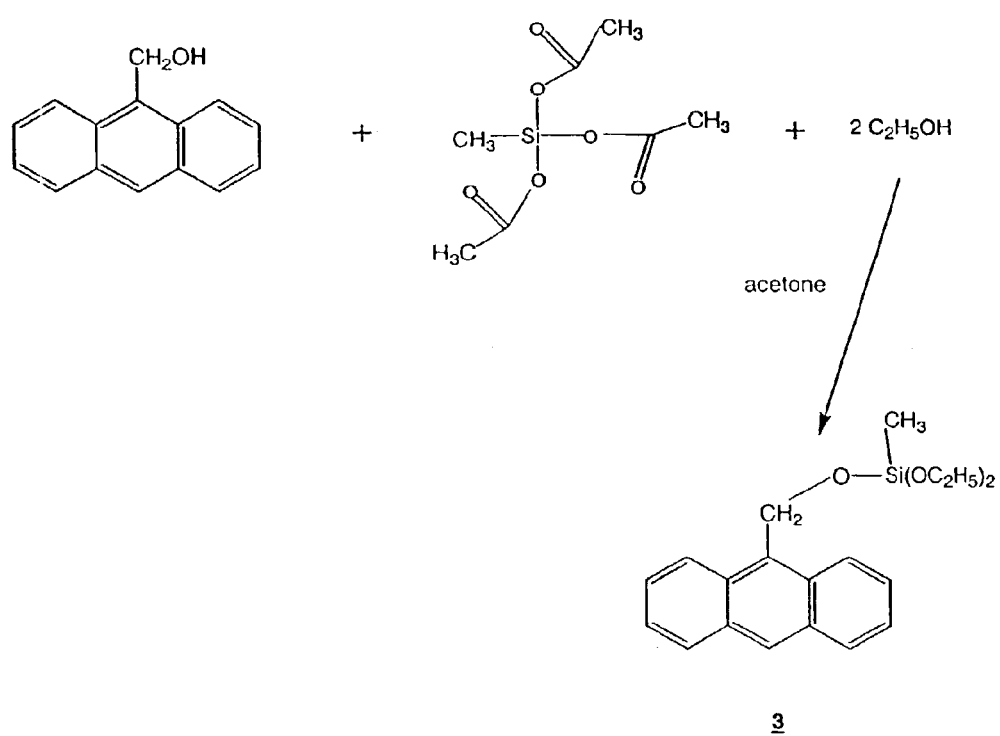
FIG. 1 depicts the reaction scheme for synthesizing 9-anthracene methoxy-methyldiethoxysilane using meythyltriacetoxysilane, according to an embodiment of the present invention.

An anti-reflective coating material for deep ultraviolet photolithography includes one or more organic absorbing compounds incorporated into a spin-on-glass (SOG) material. The absorbing spin-on-glass compositions are dissolved in appropriate solvents to form coating solutions and applied to various layers of materials in fabricating semiconductor devices. The absorbing spin-on-glass anti-reflective coatings have been designed to be readily integrated into existing semiconductor fabrication processes. Properties that provide integration include developer resistance, thermal stability during standard photoresist processing, and selective removal with respect to underlying layers.

Many naphthalene- and anthracene-based compounds have significant absorption at 248 nm and below. Benzene-based, equivalently termed here phenyl-based, compounds have significant absorption at wavelengths shorter than 200 nm. While these naphthalene-, anthracene-, and phenyl-based compounds are frequently referred to as dyes, the term absorbing compound is used here because the absorptions of these compounds are not limited to wavelengths in the visible region of the spectrum. However, not all such absorbing compounds can be incorporated into spin-on-glasses for use as ARC materials. Absorbing compounds suitable for use with the present invention have an absorption peak over at least an approximately 10 nm wide wavelength range around wavelengths such as 248 nm, 193 nm, or other ultraviolet wavelengths, such as 365 nm, that may be used in photolithography. Absorbing compounds which only have narrow absorption peaks, for example, less than 2 nm wide, around these wavelengths are not as desirable.

The chromophores of suitable absorbing compounds typically have one, two, or three benzene rings that may or may not be fused. Incorporatable absorbing compounds have an accessible reactive group attached to the chromophore, the reactive groups including hydroxyl groups, amine groups, carboxylic acid groups, and substituted silyl groups with silicon bonded to one, two, or three "leaving groups," such as alkoxy groups or halogen atoms. Ethoxy or methoxy groups or chlorine atoms are frequently used as leaving groups. Thus, suitable reactive groups include siliconethoxy, silicondiethoxy, silicontriethoxy, siliconmethoxy, silicondimethoxy, silicontrimethoxy, chlorosilyl, dichlorosilyl, and trichlorosilyl groups. Specific examples of incorporatable absorbing compounds for spin-on glass compositions are described in U.S. patent application Ser. No. 09/491,166, which is commonly assigned with the present application and incorporated herein by reference. The inclusion of reactive groups with one or more ethoxy groups bonded to silicon has been found to be advantageous, especially for promoting thermal stability of the absorbing SOG films.

According to an aspect of the present invention, an incorporatable absorbing compound includes a siliconethoxy, silicondiethoxy, or silicontriethoxy species as a reactive group attached to a naphthalene or anthracene chromophore via an oxygen linkage. Thus, the absorbing compounds of the present invention are ether-like. (If the silicon atom in the absorbing compound were replaced by a carbon atom, the compounds would be strictly classified as ethers.) The compounds may have the general structure

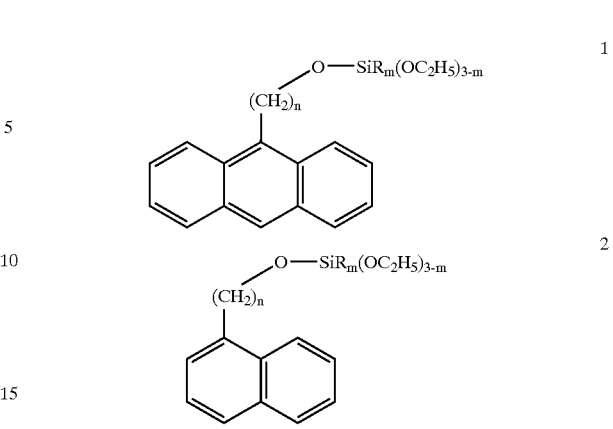

where n=1–3, m=0–2, and R is hydrogen or an alkyl group such as a methyl, ethyl, or propyl group. Structures 1 and 2 illustrate compounds in which the reactive group is attached to the chromophore at a particular substituent site. Analogous compounds in which reactive groups are attached to alternative sites, all described by the general formulas $C_{14}H_9(CH_2)_nOSiR_m(OC_2H_5)_{3-m}$ or $C_{10}H_8(CH_2)_nOSiR_m(OC_2H_5)_{3-m}$ are also included in the present invention.

A method of synthesizing the light-absorbing ether-like compounds of structures 1 and 2 is based on the reaction of an alcohol-substituted fused ring chromophore with an acetoxysilicon compound in the presence of alcohol. The acetoxysilicon reactant is given by the general formula $R_mSi(OCOCH_3)_{4-m}$, where R and m are defined above. Particular examples of useful acetoxysilicon compounds include methyltriacetoxysilane (MTAS), tetraacetoxysilane (TAS), dimethyldiacetoxysilane, and diethyldiacetoxysilane. Useful alcohols include methanol, ethanol, and propanol.

For example the synthesis of 9-anthracene methoxymethyldiethoxysilane 3

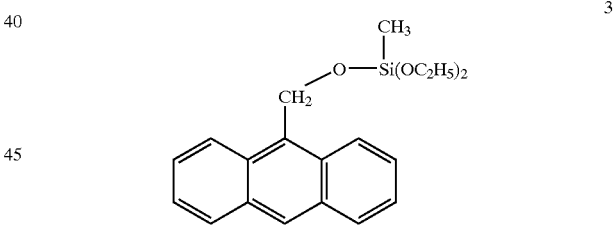

uses 9-anthracene methanol, MTAS, and ethanol in a molar ratio of 1:1:2 as reactants. As can be understood from the reaction mechanism of FIG. 1, one acetoxy group on MTAS reacts with the —CH$_2$OH on 9-anthracene methanol to form the ether linkage to the silicon-containing reactive group and acetic acid while two acetoxy groups on MTAS react with ethanol to form the ethoxy group and acetic acid. In the synthesis method, the reactants are combined with acetone, or an alternative ketone such as methylisobutylketone (MIBK) or methylethylketone, to form a reaction mixture which is stirred for an extended period sufficient to form the product 3, typically several days, and then the acetic acid byproduct is removed by purging with inert gas or by vacuum extraction. From this reaction mechanism, it may be understood that in general, the ratio of alcohol-substituted fused ring compound to acetoxysilicon compound, $R_mSi(OCOCH_3)_{4-m}$, to alcohol is 1:1:3-m.

The absorbing ether-like compounds may be incorporated in spin-on-glass materials including methylsiloxane, methylsilsesquioxane, phenylsiloxane, phenylsilsesquioxane, methylphenylsiloxane, methylphenylsilsesquioxane, and silicate polymers. As used herein, spin-on-glass materials also include hydrogensiloxane polymers of the general formula $(H_{0-1.0}SiO_{1.5-2.0})_x$ and hydrogensilsesquioxane polymers, which have the formula $(HSiO_{1.5})_x$, where x is greater than about 8. Also included are copolymers of hydrogensilsesquioxane and an alkoxyhydridosiloxane or hydroxyhydridosiloxane. Spin-on-glass materials additionally include organohydridosiloxane polymers of the general formula $(H_{0-1.0}SiO_{1.5-2.0})_n(R'_{0-1.0}SiO_{1.5-2.0})_m$, and organohydridosilsesquioxane polymers of the general formula $(HSiO_{1.5})_n(R'SiO_{1.5})_m$, where m is greater than 0 and the sum of n and m is greater than about 8 and R' is alkyl or aryl. Some useful organohydridosiloxane polymers have the sum of n and m from about 8 to about 5000 where R' is a $C_1$–$C_{20}$ alkyl group or a $C_6$–$C_{12}$ aryl group. The organohydridosiloxane and organohydridosilsesquioxane polymers are alternatively denoted spin-on-polymers. Specific examples include methylhydridosiloxanes, ethylhydridosiloxanes, propylhydridosiloxanes, t-butylhydridosiloxanes, phenylhydridosiloxanes, methylhydridosilsesquioxanes, ethylhydridosilsesquioxanes, propylhydridosilsesquioxanes, t-butylhydridosilsequioxanes, phenylhydridosilsesquioxanes, and combinations, thereof.

In the absorbing spin-on-glass, compositions, the absorbing compounds may be incorporated interstitially in the spin-on-glass matrix. Alternatively, the absorbing compounds are chemically bonded to the spin-on-glass polymer. Without being bound to any theory, the inventors suggest that bonding of incorporatable absorbing compounds to the spin-on-glass polymer backbone via the accessible reactive groups provides beneficial results.

Spin-on-glass materials are typically synthesized from a variety of silane reactants including, for example, triethoxysilane (HTEOS), tetraethoxysilane (TEOS), methyltriethoxysilane (MTEOS), dimethyldiethoxysilane, dimethyldimethoxysilane, tetramethoxysilane (TMOS), methyltrimethoxysilane (MTMOS), trimethoxysilane, dimethyldimethoxysilane, phenyltriethoxysilane (PTEOS), phenyltrimethoxysilane (PTMOS), diphenyldiethoxysilane, and diphenyldimethoxysilane. Halosilanes, particularly chlorosilanes such as trichlorosilane, methyltrichlorosilane, ethyltrichlorosilane, phenyltrichlorosilane, tetrachlorosilane, dichlorosilane, methyldichlorosilane, dimethyldichlorosilane, chlorotriethoxysilane, chlorotrimethoxysilane, chloromethyltriethoxysilane, chloroethyltriethoxysilane, chlorophenyltriethoxysilane, chloromethyltrimethoxysilane, chloroethyltrimethoxysilane, and chlorophenyltrimethoxysilane are also used as silane reactants. To produce absorbing spin-on-glass compositions, the absorbing ether compounds, such as structures (1) or (2), or combinations of structures (1) and/or (2) and other absorbing compounds, are combined with the silane reactants during the synthesis of the SOG materials.

In a typical method of producing an absorbing spin-on glass composition, a reaction mixture including silane reactants, for example HTEOS, or TEOS and MTEOS, or, TMOS and MTMOS; or, alternatively, tetrachlorosilane and methyltrichlorosilane, one or more absorbing compounds; a solvent or combination of solvents; and an acid/water mixture, is formed in a reaction vessel. Appropriate solvents include acetone, 2-propanol, and other simple alcohols, ketones and esters such as 1-propanol, MIBK, propoxypropanol, and propyl acetate. The acid/water mixture is, for example nitric acid and water. Other protic acids or acid anhydrides, such as acetic acid, formic acid, phosphoric acid, hydrochloric acid or acetic anhydride are alternatively used in the acid mixture. The resulting mixture is held at a temperature between about 30 and 80° C. for between approximately 1 and 24 hours to produce the absorbing SOG polymer solution.

The absorbing SOG can be diluted with appropriate solvents to achieve coating solutions that produce films of various thicknesses. Suitable dilutant solvents include acetone, 2-propanol, ethanol, butanol, methanol, propylacetate, ethyl lactate, propylene glycol methyl ether acetate, and propylene glycol propyl ether, referred to commercially as Propasol-P. Dilutant solvents with high boiling points such as ethyl lactate and propylene glycol propyl ether have been found to be beneficial. It is believed high boiling point solvents decrease the probability of formation of bubble film defects. In contrast, lower boiling point solvents may become entrapped below a crosslinked top layer of a film and subsequently produce voids when driven off during a baking process step. Additional solvents useful in the invention include ethylene glycol dimethyl ether, alternatively termed glyme, anisole, dibutyl ether, dipropyl ether, and pentanol. Optionally, surfactants, such as the product FC430, provided by 3M (Minneapolis, Minn.), or the product Megaface R08, provided by DIC (Japan), are also added to the coating solution. The coating solution is typically between about 0.5 and 20% polymer by weight. Prior to use, the coating solution is filtered by standard filtration techniques.

A method of forming an absorbing organohydridosiloxane material includes forming a mixture of a dual phase solvent which includes both a non-polar solvent and a polar solvent and a phase transfer catalyst; adding one or more organotrihalosilane, hydridotrihalosilane, and one or more of absorbing compounds, to provide a dual phase reaction mixture; and reacting the dual phase reaction mixture for between 1 and 24 hours to produce the absorbing organohydridosiloxane polymer. The phase transfer catalyst includes but is not limited to tetrabutylammonium chloride and benzyltrimethylammonium chloride. Exemplary non-polar solvents include, but are not limited to, pentane, hexane, heptane, cyclohexane, benzene, toluene, xylene, halogenated solvents such as carbon tetrachloride and mixtures thereof. Useful polar solvents include water, alcohols, and alcohol and water mixtures. The absorbing polymer solution is diluted and filtered as described above to form a coating solution.

The absorbing SOG coating solutions are applied to various layers used in semiconductor processing, depending on the specific fabrication process, typically by conventional spin-on deposition techniques. These techniques include a dispense spin, a thickness spin, and thermal bake steps, to produce an absorbing SOG anti-reflective film. Typical processes include a thickness spin of between 1000 and 4000 rpm for about 20 seconds and two or three bake steps at temperatures between 80° C. and 300° C. for about one minute each. As reported in Example 2 below, an absorbing SOG anti-reflective film with absorbing ether of structure (3) exhibits an extinction coefficient greater than 0.18.

The methods of synthesizing 9-anthracene methoxy-methyldiethoxysilane 3, 9-anthracene methoxy-triethoxysilane and the absorbing SOG material including these absorbing compounds are described in the following examples.

EXAMPLE 1

Synthesis of 9-anthracene methoxy-methyldiethoxysilane

In a 3 liter flask, 92.37 grams (0.419 moles) methyltriacetoxysilane (MTAS), 87.36 grams (0.419 moles) 9-anthracene methanol, 38.56 grams (0.839 moles) ethanol, 595.51 grams (10.20 moles) acetone were combined. The solution was stirred in a nitrogen atmosphere for 7 days. The solution was degassed to remove the acetic acid byproduct.

EXAMPLE 2

Synthesis of Absorbing SOG Containing 9-anthracene methoxy-methyldiethoxysilane

In a 1-liter flask 297 grams (4.798 moles), 2-Propanol, 148 grams (2.558 moles) acetone, 123 grams (0.593 moles) TEOS, 77 grams (0.432 moles) MTEOS, 200 g 9-anthracene methoxy-methyldiethoxysilane, produced in Example 1, 2.61 grams (0.009) moles rosolic acid, 10 grams (0.024 moles) 2-hydroxy-4(3-triethoxysilylpropoxy)-diphenylketone, 0.09 grams (0.0004 moles) anthraflavic acid, 0.6 grams 1.0 M nitric acid and 72 grams (3.716 moles) deionized water were combined. The flask was refluxed for 4 hours. To the solution, 43 grams (0.590 moles) of butanol was added. The solution was filtered. The solution was dispensed, followed by a 3000 rpm thickness spin for 20 seconds, and baked at 80° C. and at 180° C. for one minute each. Optical properties were measured with an N & K Technology Model 1200 analyzer. The film thickness was 2801 Å. At 248 nm, the refractive index (n) was 1.470 and the extinction coefficient (k) was 0.185.

EXAMPLE 3

Synthesis of 9-anthracene methoxy-triethoxysilane

In a 3 liter flask, 110.73 grams (0.419 moles) tetra-acetoxysilane (TAS), 87.36 grams (0.419 moles) 9-anthracene methanol, 57.98 grams (1.2585 moles) ethanol, 595.51 grams (10.20 moles) acetone are combined. The solution is stirred in a nitrogen atmosphere for 7 days. The solution is degassed to remove the acetic acid byproduct.

EXAMPLE 4

Synthesis of Absorbing SOG Containing 9-anthracene methoxy-triethoxysilane

In a 1-liter flask 297 grams (4.798 moles), 2-Propanol, 148 grams (2.558 moles) acetone, 123 grams (0.593 moles) TEOS, 77 grams (0.432 moles) MTEOS, 200 g 9-anthracene methoxy-triethoxysilane, produced in Example 3, 0.6 grams 1.0 M nitric acid and 72 grams (3.716 moles) deionized water are combined. The flask is refluxed for 4 hours. To the solution, 43 grams (0.590 moles) of butanol is added. The solution is filtered.

EXAMPLE 5

Synthesis of Absorbing SOG Containing 9-anthracene methoxy-methyldiethoxysilane

In a 1-liter flask 297 grams (4.798 moles), 2-Propanol, 148 grams (2.558 moles) acetone, 123 grams (0.593 moles) TEOS, 77 grams (0.432 moles) MTEOS, 200 g 9-anthracene methoxy-methyldiethoxysilane, produced in Example 1, 0.6 grams 1.0 M nitric acid and 72 grams (3.716 moles) deionized water are combined. The flask is refluxed for 4 hours. To the solution, 43 grams (0.590 moles) of butanol is added. The solution is filtered.

Although the invention has been described with reference to particular examples, the description is only an example of the invention's application and should not be taken as a limitation. Various adaptations and combinations of features of the examples disclosed are within the scope of the invention as defined by the following claims.

We claim:

1. A light-absorbing spin-on composition, comprising:

a spin-on glass material; and an incorporatable absorbing compound, wherein the absorbing compound comprises a silicon-containing moiety, an oxygen linkage to the silicon-containing moiety and at least one benzene ring.

2. The composition of claim 1, wherein the incorporatable absorbing compound has the formula $C_{14}H_9(CH_2)_nOSiR_m(OC_2H_5)_{3-m}$ or $C_{10}H_8(CH_2)_nOSiR_m(OC_2H_5)_{3-m}$, wherein n=1–3, m=0–2, and R is selected from the group consisting of hydrogen, methyl, ethyl, and propyl.

3. The composition of claim 2, wherein the incorporatable absorbing compound is 9-anthracene methoxy-methyldiethoxysilane.

4. The composition of claim 2, wherein the spin-on glass material is a siloxane polymer.

5. The composition of claim 4, wherein the siloxane polymer is a polymer comprising methysiloxane, methylsilsesquioxane, phenylsiloxane, phenylsilsesquioxane, methyiphenylsiloxane, methylphenylsilsesquioxane, and silicate polymers.

6. The composition of claim 4, wherein the siloxane polymer is a polymer comprising hydrogensiloxane, hydrogensilsesquioxane, organohydridosiloxane, and organohydridosilsesquioxane polymers; and copolymers of hydrogensilsesquioxane and an alkoxyhydridosiloxane or hydroxyhydridosiloxane.

7. The composition of claim 6, wherein the siloxane polymer is a polymer of a general formula comprising $(H_{0-1.0}SiO_{1.5-2.0})_x$, where x is greater than about 8, and $(H_{0-1.0}SiO_{1.5-2.0})_n(R'_{0-1.0}SiO_{1.5-2.0})_m$, where m is greater than 0, the sum of n and m is from about 8 to about 5000 and R' is a $C_{1-20}$ alkyl group or a $C_6$–$C_{12}$ aryl group.

8. The composition of claim 1, wherein the silicon-containing moiety comprises siliconethyoxy, silicondietheoxy, and silicontriethoxy.

9. The composition of claim 1, wherein at least part of the spin-on glass composition can be selectively removed.

10. The composition of claim 1, wherein the at least one benzene ring comprises two or three fused benzene rings.

11. An incorporatable ether-like absorbing compound, comprising a siliconalkoxy moiety, at least one benzene ring and an oxygen linkage to the siliconalkoxy moiety, wherein the siliconalkoxy moiety comprises the formula $C_{14}H_9(CH_2)_nOSiR_m(OC_2H_5)_{3-m}$ or $C_{10}H_8(CH_2)_nOSiR_m(OC_2H_5)_{3-m}$, wherein n=1–3, m=0–2, and R is selected from the group consisting of hydrogen, methyl, ethyl, and propyl.

12. The compound of claim 11, wherein the absorbing compound is 9-anthracene methoxy-methyldiethoxysilane.

13. The compound of claim 11, wherein the siliconalkoxy moiety comprises siliconethyoxy, silicondietheoxy, and silicontriethoxy.

14. The compound of claim 11, wherein the at least one benzene ring comprises two or three fused benzene rings.

15. The compound of claim 11, wherein the compound comprises an absorption peak over at least an about 10 nm wide wavelength range.

16. The compound of claim 15, wherein the absorption peak comprises a wavelength that is in the deep ultraviolet wavelength portion of the spectrum.

* * * * *